US006818621B2

(12) United States Patent
Ashkar

(10) Patent No.: US 6,818,621 B2
(45) Date of Patent: Nov. 16, 2004

(54) OSTEOPONTIN-DERIVED CHEMOTACTIC AND INHIBITORY AGENTS AND USES THEREFOR

(75) Inventor: Samy Ashkar, Boston, MA (US)

(73) Assignee: Children's Medical Center Corporation, Boston, MA (US)

(*) Notice: Subject to any disclaimer, the term of this patent is extended or adjusted under 35 U.S.C. 154(b) by 603 days.

(21) Appl. No.: 09/729,873

(22) Filed: Dec. 5, 2000

(65) Prior Publication Data

US 2001/0036921 A1 Nov. 1, 2001

Related U.S. Application Data

(60) Provisional application No. 60/129,764, filed on Apr. 15, 1999.

(51) Int. Cl.$^7$ ............................................... A61K 38/00

(52) U.S. Cl. ........................ 514/17; 530/329; 530/330

(58) Field of Search ......................... 514/17; 530/330, 530/329; 424/130.1

(56) References Cited

U.S. PATENT DOCUMENTS

| 4,187,852 A | 2/1980 | Urry et al. |
| 4,280,954 A | 7/1981 | Yannas et al. |
| 4,683,195 A | 7/1987 | Mullis et al. |
| 4,758,512 A | 7/1988 | Goldberg et al. |
| 4,939,239 A | 7/1990 | Matsuhashi et al. |
| 5,049,659 A | 9/1991 | Cantor et al. |
| 5,238,839 A | 8/1993 | Cantor et al. |
| 6,686,444 B2 * | 2/2004 | Ashkar ....................... 530/329 |

FOREIGN PATENT DOCUMENTS

| WO | WO 98/07750 | 2/1998 |
| WO | WO 99/08730 | 2/1999 |

OTHER PUBLICATIONS

Marshall, V., Peterson, M., Lew, A., and Kemp, D. Structure of the apical membrane antigen I (AMA–1) of *Plasmodium chabaudi*. Molecular and Biochemical Parasitology, 37 (1989) 281–284.*
Weber G., Ashkar, S., Glimcher, M., and Cantor, H. Receptor–Ligand Interaction Between CD44 and Osteopontin (Eta–1). Science 271 (1996) 509–512.*
Amann, et al., "Tightly regulated tac promoter vectors useful for the expression of unfused and fused proteins in *Escherichia coli*," *Gene* 69:301–315 (1988).
Baldari, et al., "A novel leader peptide which allows efficient secretion of a fragment of human interleukin 1 beta in *Saccharomyces cerevisiae*," *Embo J.* 6:229–234 (1987).
Berkowitz, et al., *Surgery*, 72, 221 (1972).
Boggio, et al., "Interleukin 12–mediated prevention of spontaneous mammary adenocarcinomas in two lines of Her–2/neu transgenic mice." *Exp. Med* 188(3): 589–596 (1998).

Dagalakis, et al., "Design of an artificial skin. Part III. Control of pore structure," *J. Biomed Mater. Res.* 14(4): 511–528 (1980).
Dann, et al., "Human renin: a new class of inhibitors," *Biochem Biophys Res Commun* 134(1): 71–7 (1986).
Ewenson, et al., "Ketomethylene pseudopeptide analogues of substance P: synthesis and biological activity," *J Med Chem* 29(2):295–9 (1986).
Giachelli, et al., "Molecular cloning and characterization of 2B7, a rat mRNA which distinguishes smooth muscle cell phenotypes in vitro and is identical to osteopontin (secreted phosphoprotein I, 2aR)," *Biochem Biophys Res Commun* 177(2):867–73 (1991).
Goldfarb, et al., "Graphite–expanded polytetrafluoroethylene: an improved small artery prosthesis," *Trans Am. Soc. Art. Int. Org.* 23: 268–276 (1977).
Gordon, et al., "Design of peptide derived amino alcohols as transition–state analog inhibitors of angiotensin converting enzyme," *Biochem Biophys Res Commun* 126(1):419–26 (1985).
Ho, et al., "Site–directed mutagenesis by overlap extension using the polymerase chain reaction," *Gene*, 77(1): 51–59 (1989).
Hochuli, et al., *Bio/Technology* 6:1321–1325 (1988).
Hostomsky, et al., "High–level expression of self–processed HIV–1 protease in *Escherichia coli* using a synthetic gene," *Biochem. Biophys, Res. Commun.*, 161(3): 1056–1063 (1989).
Hwang, et al., "Osteopontin inhibits induction of nitric oxide synthase gene expression by inflammatory mediators in mouse kidney epithelial cells," *J. Biol. Chem.* 269: 711–715 (1994).
Jameel, et al., "Hepatitis B virus X protein produced in *Escherichia coli* is biologically functional," *J Virol* 64(8):3963–6 (1990).
Janseen & Van Den Berge. *Cancer Res.* 58(24): 5646–8 (1998).
Katagiri, et al., "CD44 variants but not CD44s cooperate with beta 1–containing integrins to permit cells to bind to osteopontin independently of arginine–glycine–aspartic acid, thereby stimulating cell motility and chemotaxis," *Cancer Res* 59(1):219–26 (1999).
Knapp, et al., "pSEM vectors: high level expression of antigenic determinants and protein domains," *Biotechniques* 8(3):280–1 (1990).
Kurjan, et al., "Structure of a yeast pheromone gene (MF alpha): a putative alpha–factor precursor contains four tandem copies of mature alpha–factor," *Cell* 30(3): 933–943 (1982).

(List continued on next page.)

*Primary Examiner*—Karen Cochrane Carlson
*Assistant Examiner*—Anand Desai
(74) *Attorney, Agent, or Firm*—Pabst Patent Group LLP

(57) ABSTRACT

Novel osteopontin-derived chemotactic and inhibitory agents are described. Methods of using these agents are also described.

6 Claims, No Drawings

OTHER PUBLICATIONS

Manzano, et al., "Tretinoin prevents age–related renal changes and stimulates antioxidant defenses in cultured renal mesangial cells," *J Pharmacol Exp Ther* 289(1):123–32 (1999).

Marsh, "Preparation and properties of ,allergoids, derived from native pollen allergens by mild formalin treatment," *International Archives of Allergy and Applied Immunology*, 41(1): 199–215 (1971).

Matteucci, et al., J. Am. Chem. Soc., 103:3185 (1981).

Nagai, et al., *Tetrahedron Lett*. 26:647 (1985).

Oldberg, et al., "Identification of a bone sialoprotein receptor in osteosarcoma cells ," *J. Biol Chem* 263(36):19433–6 (1988).

Oldberg, et al., "Cloning and sequence analysis of rat bone sialoprotein (osteopontin) cDNA reveals an Arg–Gly–Asp cell–binding sequence," *Proc. Natl Acad Sci U S A* 83(23):8819–23 (1986).

Patarca, et al., "Structural and functional studies of the early T lymphocyte activation 1 (Eta–1) gene. Definition of a novel T cell–dependent response associated with genetic resistance to bacterial infection," *J Exp Med* 170(1):145–61 (1989).

Patarca, et al., "Differential induction of interferon gamma gene expression after activation of CD4+ T cells by conventional antigen and Mls superantigen," *Proc Natl Acad Sci U S A* 88(7):2736–9 (1991).

Rizo, et al., "Constrained peptides: models of bioactive peptides and protein substructures," *Annu Rev Biochem* 61:387–418 (1992).

Rovin, et al., "Chemotactic factors and renal inflammation," *Am J Kidney Dis* 31(6):1065–84 (1998).

Sato, et al., *J Chem. Soc. Perkin. Trans*. 1:1231 (1986).

Schultz, et al., "Expression and secretion in yeast of a 400–kDa envelope glycoprotein derived from Epstein–Barr virus," *Gene* 54(1): 113–123 (1987).

Senger, et al., "Elevated expression of secreted phosphoprotein I (osteopontin, 2ar) as a consequence of neoplastic transformation," *Anticancer Res* 9(5):1291–9 (1989).

Singh, et al., "Definition of a specific interaction between the early T lymphocyte activation 1 (Eta–1) protein and murine macrophages in vitro and its effect upon macrophages in vivo," *J. Exp. Med* 171(6):1931–1942 (1990).

Smith, et al., "Molecular cloning of a tumor promoter–inducible mRNA found in JB6 mouse epidermal cells: induction is stable at high, but not at low, cell densities," *J Cell Biochem* 34(1):13–22 (1987).

Strejan, et al., "Suppression of chronic–relapsing experimental allergic encephalomyelitis in strain–13 guinea pigs by administration of liposome–associated myelin basic protein," *J Neuroimmunol* 7(1):27–41 (1984).

Wagner, et al., *J. Surg. Res*., 1, 52 (1956).

Weber, et al., "Receptor–ligand interaction between CD44 and osteopontin (Eta–1)," *Science* 271(5248):509–12 (1996).

Wie, et al., "Suppression of reaginic antibodies with modified allergens. III. Preparation of tolerogenic conjugates of common allergens with monomethoxypolyethylene glycols of different molecular weights by the mixed anhydride method," *Int Arch Allergy Appl Immunol* 64(1):84–99 (1981).

Wrana, et al., "Full length cDNA sequence of porcine secreted phosphoprotein–I (SPP–1, osteopontin)," *Nucl. Acid. Res*. 17(23):10119 (1989).

Yannas, et al., "Design of an artificial skin. I Basic design principles," *J. Biomed. Mat. Res*. 14(1): 65–81 (1980).

Yannas, et al., "Design of an artificial skin. II. Control of chemical composition," *J Biomed Mater Res* 14(2):107–32 (1980).

\* cited by examiner

```
                            SEQUENCE LISTING

<160> NUMBER OF SEQ ID NOS:  25

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 1

Leu Val Leu Asp Pro Lys
  1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 2

Lys Phe His Ser His Lys Asp Lys Leu Val Leu Asp Pro Lys Ser Lys
  1               5                  10                  15

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 3

Leu Val Val Asp Pro Lys
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 4

Leu Val Pro Asp Pro Lys
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 5

Leu Val Pro Asp Ser Lys
  1               5
```

```
<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 6

Leu Val Ile Asp Pro Lys
  1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 7

Val Leu Asp Pro Lys
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 8

Leu Val Leu Val Pro Lys
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 9

Leu Val Pro Asp Pro Lys
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 10

Leu Val Leu Asp Glu Lys
  1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 11
```

Leu Val Leu Asp Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 12

Leu Glu Leu Asp Pro Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 13

Leu Val Leu Ala Pro Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 14

Leu Val Leu Glu Pro Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 15

Leu Val Leu Asp Pro Ala
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 16

Val Leu Glu Pro
1

<210> SEQ ID NO 17
<211> LENGTH: 7
<212> TYPE: PRT
<213> ORGANISM: Artificial Sequence

```
<220> FEATURE:
<223> OTHER INFORMATION: Description of Artificial Sequence:Synthetic
      Peptide

<400> SEQUENCE: 17

Ile Leu Val Val Asp Pro Lys
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 18

Val Val Leu Asp Pro Lys
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 19

Ile Leu Val Asp Pro Lys
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 20

Leu Leu Val Asp Pro Lys
  1               5

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 21

Val Asp Pro Lys
  1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 22

Val Leu Asp Ser Lys
  1               5
```

```
<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:Synthetic
      Peptide
<221> NAME/KEY: MOD_RES
<222> LOCATION: (1)
<223> OTHER INFORMATION: ACETYLATION

<400> SEQUENCE: 23

Leu Val Leu Asp Pro
 1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide
<221> NAME/KEY: MOD_RES
<222> LOCATION: (1)
<223> OTHER INFORMATION: ACETYLATION

<400> SEQUENCE: 24

Met Leu Asp Pro
 1

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide
<221> NAME/KEY: MOD_RES
<222> LOCATION: (1)
<223> OTHER INFORMATION: ACETYLATION

<400> SEQUENCE: 25

His Lys Asp Lys Met Leu Asp Pro
 1               5
```

OSTEOPONTIN-DERIVED CHEMOTACTIC AND INHIBITORY AGENTS AND USES THEREFOR

CROSS REFERENCE TO RELATED APPLICATIONS

This application claims the benefit of U.S. Provisional Application No. 60/129,764 filed on Apr. 15, 1999.

GOVERNMENT SUPPORT

This invention was made with government support from the National Institutes of Health. Accordingly, the government has certain rights in the invention.

BACKGROUND OF THE INVENTION

Osteopontin (Oldberg et al. (1986) *Proc. Natl. Acad. Sci. USA* 83:8819; Oldberg et al. (1986) *J. Biol. Chem.* 263:19433–19436) also known as OPN (Wrana et al. (1989) *Nucl. Acid Res.* 17:3306), 2ar (Smith and Denhardt (1987). *J. Cell Biochem.* 34:10–22), transformation-associated secreted phosphoprotein (Senger et al. (1989) *Anticancer Res.* 48:1291), or early T-lymphocyte activation-1 (Patarca et al. (1991) *Proc. Natl. Acad. Sci. USA* 88:2736), is a multifunctional secreted glycoprotein which is expressed by a wide variety of cell types including bone (Oldberg et al. (1986) *J. Biol. Chem.*, supra), smooth muscle cells (e.g., cells of the vascular system) (Giachelli et al. (1991) *Biochem. Biophys. Res. Commun.* 177: 867–873), activated T-lymphocytes (Patarca et al. (1989) *J. Exp. Med.* 170:145–161; Patarca et al. (1991) *Proc. Natl. Acad. Sci. USA*, supra), macrophages (Singh et al. (1990). *J. Exp. Med* 171:1931–1942), and carcinomas and sarcomas (Senger et al., supra). In other tissues, osteopontin is expressed during various developmental stages and circulating levels of the protein have been found to be elevated in individuals with autoimmune diseases. Osteopontin is also elevated in sera from patients with advanced metastatic cancer and cellular transformation may lead to enhanced osteopontin expression and increased metastatic activity.

The protein is involved in a range of cellular functions including cell adhesion and spreading, cell migration and homing, chemotaxis, and calcium homeostasis (e.g., calcification). Osteopontin is induced by oxidative stress, including ischemia/reperfusion, heat shock or starvation, and exerts antioxidant effects by down-regulation of inducible nitric oxide synthetase (conferring protection against killing by macrophages). Moreover, osteopontin has been found to inhibit apoptosis in various cell types and in response to a wide range of stimuli.

In mammals, osteopontin is known to play an important role in regulation of bone formation and/or bone remodeling, regulation of immune responses, mediation of inflammation (e.g., tissue inflammation) in specific disease and injury states, angiogenesis, and arterial wound healing. Osteopontin has also been shown to be secreted by malignant tumors and is believed to play an important role in metastasis formation. The protein is subject to a large number of post-translational modifications (e.g., phosphorylation) and, in fact, the considerable number of functions that have been attributed to this protein are believed to be differentially regulated by such post translational modifications.

Osteopontin binds to cells via integrin and non-integrin receptors. The presence of a Gly-Arg-Gly-Asp-Ser (GRGDS, SEQ ID NO:1) cell-surface receptor binding motif within the sequence of osteopontin is involved in cell attachment and spreading via $\alpha_v\beta_3$, $\alpha_v\beta_1$ and $\alpha_v\beta_5$ integrins (Oldberg et al., supra). Cleavage of osteopontin with thrombin enhances its cell attachment properties. A distinct receptor-ligand interaction between CD44 and osteopontin, has also been shown to play a role in mediating chemotaxis and/or cell or attachment. Multiple phosphorylated and nonphosphorylated forms of osteopontin are secreted by cells and are differentially stimulated by tumor promoters (Kubota et al. (1989) *Biochem. Biophys. Res. Commun.* 162: 1453–1459). In addition, differential attachment of osteoclasts to surfaces coated with osteopontin isolated from various tissues and to phosphorylated and nonphosphorylated osteopontin has been demonstrated.

SUMMARY OF THE INVENTION

Given the important role that osteopontin plays in cellular processes including cell spreading and chemotaxis as well as the important functions it has in diverse processes including arterial wound healing, immune response, bone development, tissue remodeling, and metastasis, there exists a need to identify peptides and develop compounds that mimic or inhibit many of the unique functions of osteopontin. In particular, there exists a need for identifying peptides and developing compounds which mimic the chemotactic activities of osteopontin as well as agents (e.g., antibodies, peptides and compounds) which are inhibitory for osteopontin-dependent chemotaxis.

The present invention is based, at least in part, on the discovery of or identification of the chemotactic regions of the naturally-occurring osteopontin protein. This discovery led to the development of chemotactic compounds and peptides derived from osteopontin. The discovery also led to the development of peptides which are inhibitory to chemotaxis. Accordingly, the compounds and peptides of the present invention can be used to induce and/or inhibit chemotaxis, either in vivo or in vitro. The compounds and peptides of the present invention can be used to treat conditions or diseases associated with chemotaxis. For example, the compounds and peptides of the present invention can be used to treat or inhibit tumor metastasis, inflammation, osteoporosis and autoimmune disease. Moreover, the compounds and peptides of the present invention have applications in angiogenesis, wound-healing and in the development of prosthetic devices.

The present invention pertains to osteopontin derived compounds and peptides. The compounds and peptides are capable of modulating (e.g., inducing or inhibiting) the chemotaxis of several cell types. Examples of cell types include, but are not limited to, endothelial cells, periosteal cells, tumor cells, macrophages and osteoprogenitor cells.

In one embodiment, the invention features purified osteopontin-derived chemotactic peptide (e.g., purified osteopontin-derived peptides having chemotactic activity). In another embodiment, the invention features purified chemotactic compounds having the following formula:

wherein Q and X are flanking moieties and are absent or present and A is a hydrophobic core constituent, forming a compound having chemotactic activity.

In another embodiment, the invention features chemotactic compounds which include a hydrophobic core constituent (A) having the following motif:

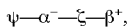

wherein ψ is a hydrophobic patch, α⁻ is an acidic moiety, ζ is a bend-forming moiety, and β⁺ is a basic moiety.

The invention also pertains to isolated nucleic acid molecules encoding the osteopontin derived peptides of the present invention which can be used to produce the peptides and also as a therapeutic agent. Likewise, the invention pertains to antibodies (e.g., monoclonal antibodies) which specifically react with osteopontin-derived peptides. These antibodies can be administered to a subject in the form of a therapeutic composition to modulate the chemotactic effect of the peptides of the invention, thus neutralizing the migration of various cell types in response to osteopontin.

In another aspect, the invention features a therapeutic composition which includes an chemotactic compound, chemotactic peptide, inhibitory compound or peptide and a pharmaceutically-acceptable carrier or diluent. The therapeutic composition can be used in the methods described herein.

In another aspect, the invention features a method for modulating tumor invasion or tumor metastasis in a subject. In one embodiment, the method includes administering to a subject (e.g., at a tumor site) a therapeutically effective amount of an inhibitory compound, or a chemotactic peptide antibody, such that tumor invasion or tumor metastasis is modulated. In another embodiment, the method includes administering to a subject (e.g., at a tumor site) a therapeutically effective amount of an inhibitory compound complexed to a carrier (e.g., an extracellular matrix molecule, for example, collagen, glycosamoniglycans, for example, hyaluronic acid, chondroitin sulfates and heparan sulfates), such that tumor metastasis is modulated (e.g., inhibited).

In another aspect, the invention features a method for modulating nitrous oxide production in a cell or subject. In one embodiment, the method includes contacting a cell with an effective amount of a chemotactic peptide of the present invention (or an effective amount of an inhibitory peptide), such that nitrous oxide production is modulated (e.g., stimulated or inhibited, respectively). In another embodiment, the method includes administering to a subject a therapeutically effective amount of an chemotactic peptide or inhibitory compound such that nitrous oxide production is modulated (e.g., stimulated or inhibited, respectively).

In another aspect, the invention features a method for activating apoptosis in a cell or subject. In one embodiment, the method includes contacting a cell with an effective amount of a chemotactic peptide of the present invention such that apoptosis of the cell is activated. In another embodiment, the method includes administering to a subject a therapeutically effective amount of a chemotactic peptide such that apoptosis is activated (e.g., apoptosis of a cell(s) within the subject).

In another aspect, the invention features a method for promoting wound healing (e.g., scarless wound healing) in a subject. The method includes administering to a subject a therapeutically effective amount of a composition comprising an chemotactic compound or peptide and a pharmaceutically-acceptable carrier or diluent such that wound healing is promoted.

In another aspect, the invention features a method for promoting cell migration (e.g., cellular chemotaxis) to a target site. In one embodiment, the method includes administering to a subject (e.g. at a target site) a therapeutically effective amount of a chemotactic compound or peptide such that migration (e.g., cellular chemotaxis) of a desired cell to the target site is promoted. In another embodiment, the method includes administering at the target site, a chemotactic peptide or compound adhered to a substrate (e.g., an extracellular matrix components, for example, collagen, or glycosamoniglycans, including hyaluronic acid, chondroitin sulfates and heparan sulfates). In yet another embodiment, the method Includes coating a physical material (e.g., plastic, polyvinyl surface, steel, glass, polymer, PGA, metals, for example, titanium) with a chemotactic peptide prior to introducing the material to a subject, such that cell migration (e.g., cellular chemotaxis) is promoted.

In another aspect, the invention features a method for promoting cell migration (e.g., cellular chemotaxis) to a target site. In one embodiment, the method includes administering to a subject (e.g., at a target site) a therapeutically effective amount of a chemotactic compound or peptide such that migration (e.g., cellular chemotaxis) of a desired cell to the target site is promoted. In another embodiment, the method includes administering at the target site, a chemotactic peptide or compound adhered to a substrate (e.g., an extracellular matrix components, for ex.ample, collagen, or glycosamoniglycans. including hyaluronic acid, chondroitin sulfates and heparan sulfates). In yet another embodiment, the method includes coating a physical material (e.g., plastic, polyvinyl surface, steel, glass, polymer, PGA, metals, for example, titanium) with a chemotactic peptide prior to introducing the material to a subject, such that cell migration (e.g., cellular chemotaxis) is promoted.

In another aspect, the invention features a method for inhibiting cell migration (e.g., cellular chemotaxis) at a target site. In one embodiment, the method includes administering to a subject (e.g., at the target site) a therapeutically effective amount of an inhibitory compound or peptide or antibody such that migration (e.g., cellular chemotaxis) of a cell to the target site is inhibited. In another embodiment, the method includes administering at the target site, an inhibitory peptide or compound adhered to a substrate (e.g., an extracellular matrix components, for example, collagen, or glycosamoniglycans, including hyaluronic acid, chondroitin sulfates and heparan sulfates). In yet another embodiment, the method includes coating a physical material (e.g., plastic, polyvinyl surface, steel, glass, polymer, PGA, metals, for example, titanium) with an inhibitory peptide or compound prior to introducing the material to a subject, such that cell migration (e.g., cellular chemotaxis) is inhibited.

The invention also features a prosthetic device. The prosthetic device contains or coated with a therapeutically effective amount of a chemotactic or inhibitory compound or peptide in or on the prosthetic device.

The invention also features physical materials (e.g., plastic, polyvinyl surface, steel, glass, polymer, PGA, metals, for example, titanium) containing or coated with a therapeutically effective amount of a chemotactic or inhibitory compound or peptide.

In another aspect, the invention features a method for treating the formation of atherosclerotic plaques. The method includes administering to a subject a therapeutically effective amount of a chemotactic compound or peptide such that formation of artherosclerotic plaques is prevented.

In another aspect, the invention also features a method for treating an angiogenic-associated disease. The method includes administering to a subject a therapeutically effective amount of an antibody specifically reactive with a chemotactic peptide, or an inhibitory compound or peptide such that treatment of angiogenic-associated disease occurs.

In yet another aspect, the invention features a method of inducing in vitro chemotaxis of a cell. The method includes exposing the cell to a chemotactic compound or peptide in an amount effective to induce chemotaxis, such that chemotaxis is induced. In yet another aspect, the invention features a method of inhibiting in vitro chemotaxis of a cell. The method includes exposing the cell to an inhibitory compound or peptide in an amount effective to inhibit chemotaxis, such that chemotaxis is inhibited.

The methods of the invention are particularly useful for modulating the migration of cells (e.g., cells the movement of which it is desirable to control) involved in wound healing (e.g., extracellular matrix cells (connective tissue cells) involved in wound healing) to thereby promote recovery from wounds. The methods of the invention are particularly useful for modulating the migration of neoplastic cells (e.g., carcinoma cells, for example, of breast, testis, ovary, lung, gastrointestinal tract) to thereby modulate (e.g., inhibit) spreading from one location to another.

Antibodies specifically reactive with the chemotactic peptides of the invention or inhibitory compounds and/or peptides can also be administered to a subject having a metastatic disease (e.g., cancer) to modulate tumor invasion or to prevent or inhibit metastasis of the disease by inhibiting the chemotactic activity of osteopontin. The peptides, compounds and antibodies can be administered to the subject in the form of a therapeutic composition which includes the peptide, compound or antibody and a pharmaceutically acceptable carrier or diluent.

Other features and advantages of the invention will be apparent from the following detailed description, and from the claims.

DETAILED DESCRIPTION OF THE INVENTION

The present invention pertains, at least in part, to novel compounds and peptides (e.g., osteopontin-derived peptides) having chemotactic activity. The invention further pertains to novel osteopontin-derived inhibitory peptides and compounds (e.g., chemotaxis-inhibitory peptides and compounds). The term "osteopontin-derived" includes peptides which are substantially similar to a portion of an osteopontin protein or polypeptide. A peptide which is "substantially similar" to a portion of osteopontin includes a peptide having greater than one amino acid of which at least one amino acid is an amino acid found in the amino acid sequence of osteopontin or is similar to an amino acid found in the amino acid sequence of osteopontin. For example, osteopontin-derived peptides having two amino acids, one of which is an amino acid found in osteopontin (or is similar to an amino acid found in osteopontin), are within the scope of the present invention. Preferred osteopontin-derived peptides have at least 3, 4, 5, 6, 7, 8, 9 or 10 amino acids and have at least 2, 3, 4, 5, 6, 7, 8 or 9 amino acids found in osteopontin (or similar to an amino acids found in osteopontin). Additional preferred osteopontin-derived peptides have between 10–20, 30–40 or 50–60 amino acid residues and have at least 5–10, 15–20, 25–30, 35–40, 45–50 or 55 amino acids found in osteopontin (or similar to an amino acids found in osteopontin). As defined herein, the osteopontin-derived peptides of the present invention are not intended to include full-length osteopontin proteins or polypeptides.

In a preferred embodiment, the compounds and/or peptides (e.g., osteopontin-derived peptides) of the present invention are "chemotactic" or have a "chemotactic activity". The term "chemotactic" includes the ability of a compound or peptide to promote or induce the migration or movement of cells to or toward the peptide, either in vivo, or in vitro. Likewise, a "chemotactic activity" is a drawing or attracting of cells to or toward the peptide (or other compound), either in vivo, or in vitro. The chemotactic compounds and peptides of the present invention promote the migration of various cell types including, but not limited to eukaryotic cells, including human and/or other mammalian cells (e.g., bovine or rodent, for example mouse or rat cells). In a preferred embodiment, the compounds and/or peptides of the present invention attract cell types responsive to osteopontin (e.g., smooth muscle cells, endothelial cells, periosteal cells, macrophages and/or vascular cells).

In another preferred embodiment, the compounds and/or peptides of the present invention inhibit the attraction of cell types responsive to osteopontin (e.g., cancerous cells, for example, osteosarcoma cells, breast carcinoma cells, colon carcinoma cells, adenocarcinoma cells, and osteoprogenitor cells). In one embodiment, a chemotaxis-inhibitory peptide of the present invention has a sequence or structure which is identical to a chemotactic peptide of the present invention but lacks the basic moiety of the hydrophobic core constituent, as defined herein.

The chemotactic or inhibitory activity of a peptide or compound can be determined, for example in vitro, by determining the ability to affect (e.g., induce or inhibit) the migration of cells when assayed in a Boyden chamber assay as outlined in the Examples below. In one embodiment, a chemotactic or inhibitory activity is the ability to induce or inhibit, respectively, the migration of at least 5–10% of the cells in a given sample when assayed in a Boyden chamber assay. In another embodiment, a chemotactic or inhibitory activity is the ability to induce or inhibit, respectively, the migration of at least 20–30%, preferably at least 40–50%, more preferably at least 60–70% and even more preferably at least 80–90% of the cells in a given sample when assayed in a Boyden chamber assay as outlined in the Examples below.

The chemotactic activity of a compound or peptide can be determined, for example in vitro or in vivo, by determining an increase in the number of attracted cells at a site of introduction, treatment or application of a peptide or compound of the present invention. Likewise, the inhibitory activity of a compound or peptide can be determined, for example, in vitro or in vivo, by determining a decrease in the number of cells attracted at a site of introduction, treatment or application of a peptide or compound of the present invention. In one embodiment, a chemotactic activity is the ability to increase the number of attracted cells at a site of introduction, treatment or application by at least 5–10%. In another embodiment, a chemotactic activity is the ability to increase the number of attracted cells at a site of introduction, treatment or application by at 20–30%, preferably at least 40–50%, more preferably at least 50–70% and even more preferably at least 80–90%.

In one embodiment, the compounds and/or peptides of the present invention are "purified" compounds and/or peptides. The term "purified" includes compounds and/or peptides which have been separated from other molecules or substances which are present in the source from which the compound or peptide is derived or isolated (e.g., contaminating substances or contaminants). For example, a purified peptide can be separated from other source molecules or substances such that it is free or substantially free of source molecules or substances. In one embodiment, a peptide of the present invention is produced by recombinant DNA techniques and the purified peptide is free or substantially free or free of cellular material or culture medium. In another embodiment, a peptide or compound of the present invention is chemically synthesized and a purified peptide or compound is free or substantially free of chemical precursors or other chemicals. The language "substantially free" is defined as including preparations of the peptide or compound of interest which preferably contain less than about 50%, more preferably less than about 40%, still more preferably less than about 30%, yet more preferably less than about 20%, and most preferably less than about 10–5% of contaminating substances or contaminants.

The term "purified" further includes a peptide which exists separately from the naturally-occurring protein or polypeptide from which it was derived. For example, peptides of the present invention have at least an N-terminus or a C-terminus which is distinct from that of a naturally-occurring protein or polypeptide and preferably has both an N- and C-terminus distinct from those of a naturally-occurring protein or polypeptide.

In one embodiment, a chemotactic compound of the present invention has the formula:

wherein Q and X are flanking moieties if present (or are absent) and A is a hydrophobic core constituent. The language "hydrophobic core constituent" includes a hydrophobic (literally, 'water halting') part or portion of a compound of the present invention which allows penetration of the compound into an active site on a target molecule on which a compound of the present invention exerts its activity. In one embodiment, a "target molecule" is a receptor (e.g., a receptor which is known to bind, for example, osteopontin, e.g., a CD44 receptor). In another embodiment, a target molecule is a non-receptor protein, for example, a link protein. The language "link protein" includes a protein which causes cells to aggregate or causes complex formation between cell-surface proteins. For example, a link protein can bring the cell-surface receptor CD44 into proximity with a second cell-surface receptor, integrin, resulting in dephosphorylation of integrin and subsequent lysing of the focal adhesion, ultimately allowing a cell to form a pseudopod, involved in cell migration.

The term "flanking moiety" includes a moiety or residue which, when present in a compound or peptide of the present invention, is found adjacent to or proximal to a second or distinct moiety, residue, or constituent (e.g., a hydrophobic core constituent). A flanking moiety can contribute structurally to a compound or peptide of the present invention, for example, can result in a compound or peptide being of sufficient size to have a desired activity. Alternatively, a flanking moiety can contribute functionally to a compound or peptide of the present invention, as described further herein.

Q and A are moieties which can be present or absent. When Q and X are absent, a chemotactic compound has the size and/or structure sufficient to confer on the compound a chemotactic activity, as defined herein. Alternatively, Q and X can be present, in addition to the hydrophobic core constituent. When Q and X are present, they can contribute to the chemotactic properties of a compound of the present invention. Alternatively, Q and X, if present do not contribute to the chemotactic properties of the compound. Preferably, Q and X, if present do not detract from the chemotactic properties of the present invention. It is also within the scope of the present invention to have only Q or X present in addition to the hydrophobic core constituent.

In a preferred embodiment, the hydrophobic core constituent has the following motif:

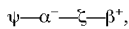

wherein $\psi$ is a hydrophobic patch, $\alpha^-$ is an acidic moiety, $\zeta$ is a bend-forming moiety, and $\beta^+$ is a basic moiety. The language "hydrophobic patch" includes a hydrophobic part or portion of the compound, e.g., a part or portion which prefers to not be in contact with water, which contributes to the hydrophobic nature of the hydrophobic core constituent. When a hydrophobic part or portion of a compound of the present invention is in contact with water, it tends to order the structure of water in the immediate vicinity, decreasing the entropy of the system. A hydrophobic patch prefers to exist in a non-aqueous environment, e.g., that found in the interior of a protein (for example, the interior of a target protein (e.g., a binding site). The release of water from the structured vicinity of the hydrophobic patch upon binding to, for example, a target binding site results in an increase in the entropy of the system, making the reaction a favorable one, also known as entropically driving the reaction. A hydrophobic patch can include, for example, amino acid residues having non-polar side chains (e.g., leucine, isoleucine, valine, methionine or alanine) or mimics or derivatives of hydrophobic residues. The term "mimic" or "derivative" includes a residue having a strong resemblance to a naturally occurring amino residue and which functions in a significantly similar manner but which has been modified structurally such that it is not identical to the naturally-occurring amino acid reside. In a preferred embodiment, a hydrophobic patch includes 1, 2, 3 or 4 hydrophobic amino acid residues, or mimics or derivatives of such residues.

The acidic moiety and basic moiety of the hydrophobic core constituent further contribute to the hydrophobic nature of the core constituent. The language "acidic moiety" includes a moiety bearing an overall or net negative charge when present in its ultimate milieu (e.g., when present within a compound or peptide, for example, a compound or peptide in a solution). The language "basic moiety" includes a moiety bearing an overall or net positive charge. The acidic and basic moieties of the hydrophobic core constituent enhance the hydrophobic nature of the core constituent by forming a bridge between the acidic and basic moieties (e.g., the acidic and basic moieties are in vicinity of each other, leading to charge stabilization of the moieties). It has been determined that the acidic/basic bridge formation is important to the overall chemotactic properties of the core constituent and is not simply a charge neutralization phenomenon, as substitution of each of an acidic moiety and a basic moiety with neutral moieties results in an inactive, as contrasted with an active compound.

The language "bend-forming moiety" includes a residue (e.g., an amino acid residue, or mimic or derivative of an amino acid residue) which is capable of introducing a bend into the backbone of the chemotactic compound of the present invention. In a preferred embodiment, a bend-forming moiety is a residue which is capable of adopting a chair conformation. For example, a bend-forming moiety can be a proline residue, a serine residue, a glycine residue, or a mimic or derivative of any of these residues.

In one embodiment, the chemotactic and/or inhibitory compounds of the present invention are peptidyl in nature. The term "peptidyl" includes compounds which more closely resemble peptides (e.g., two or more linked amino acids) and preferably, include one or more of amino acid residues. The term "non-peptidyl" includes compounds which less closely resemble peptides, and preferably include one or more or a predominance of amino acid mimics or derivatives.

In a preferred embodiment, a purified chemotactic peptide includes a portion having an amino acid sequence selected from the group consisting of LVLDPK (SEQ ID NO:1), LVVDPK (SEQ ID NO:3), LVPDPK (SEQ ID NO:4), LVPDSK (SEQ ID NO:5), LVIDPK (SEQ ID NO:6), VLDPK (SEQ ID NO:7), LVPDPK (SEQ ID NO:9), LVLEPK (SEQ ID NO:14), ILVVDPK (SEQ ID NO:17), VVLDPK (SEQ ID NO:18), ILVDPK (SEQ ID NO:19), LLVDPK (SEQ ID NO:20), VDPK (SEQ ID NO:21), and VLDSK (SEQ ID NO:22). In another preferred embodiment, a purified chemotactic peptide has an amino acid sequence selected from the group consisting of LVLDPK (SEQ ID NO:1), LVVDPK (SEQ ID NO:3), LVPDPK (SEQ ID NO:4), LVPDSK (SEQ ID NO:5), LVIDPK (SEQ ID NO:6), VLDPK (SEQ ID NO:7), LVPDPK (SEQ ID NO:9), LVLEPK (SEQ ID NO:14), ILVVDPK (SEQ ID NO:17), VVLDPK (SEQ ID NO:18), ILVDPK (SEQ ID NO:19), LLVDPK (SEQ ID NO:20), VDPK (SEQ ID NO:21), and VLDSK (SEQ ID NO:22). In yet another preferred embodiment, a purified chemotaxis-inhibitory peptide includes a portion having an amino acid sequence selected form the group consisting of LVLDP (SEQ ID NO:11), VLEP (SEQ ID NO:16), Acetyl-LVLDP (SEQ ID NO:23), Acetyl-MLDP (SEQ ID NO:24), and Acetyl-HKDKMLDP (SEQ ID NO:25). In yet another preferred embodiment, a purified chemotaxis-inhibitory peptide has an amino acid sequence selected from the group consisting of LVLDP (SEQ ID NO:11), VLEP (SEQ ID NO:16), Acetyl-LVLDP (SEQ ID NO:23), Acetyl-MLDP (SEQ ID NO:24), and Acetyl-HKDKMLDP (SEQ ID NO:25).

In one embodiment, the chemotactic compounds or peptides are not osteopontin-derived. In another embodiment, the chemotactic compounds or peptides are not those described in aformentioned pending applications (specifically or generically) U.S. Ser. No. 08/918,189 filed Aug. 21, 1997 or U.S. Provisional Application No. 60/023,427 filed Aug. 22, 1996 the contents of each are expressly incorporated by reference.

Osteopontin-derived peptides of the present invention can be synthesized by any of the techniques that are known to one of ordinary skill in the art of peptide synthesis.

Alternatively, the peptides of the present invention can be produced by recombinant DNA techniques in a host cell transformed with a nucleic acid having a sequence encoding such peptide. To produce a peptide by recombinant techniques, host cells (e.g., bacterial cells such as E. coli, insect cells, yeast, or mammalian cells, for example, Chinese hamster ovary (CHO) cells) are transformed with a vector suitable for expressing a peptide of the invention and cultured in a medium such that the cells produce the peptides. Peptides so-produced can be purified from cell culture medium, host cells, or both using techniques known in the art for purifying peptides including ultrafiltration, ion-exchange chromatography, gel filtration chromatography, electrophoresis or immunopurification with antibodies specific for the peptide.

Accordingly, the present invention provides nucleic acid molecules which encode the peptides of the present invention, expression vectors and host cells suitable for expression of such peptides. Nucleic acid coding for the peptides of the invention can easily be synthesized by chemical techniques, for example, the phosphotriester method of Matteucci et al., J. Am. Chem. Soc., 103:3185 (1981). Moreover, by chemically synthesizing the coding sequence, modifications can be made by substituting the appropriate bases for those encoding the native amino acid residue sequence.

Suitable expression vectors, promoters, enhancers, and other expression control elements may be found in Sambrook et al. *Molecular Cloning: A Laboratory Manual,* second edition, Cold Spring Harbor Laboratory Press, Cold Spring Harbor, N.Y., 1989. Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSec1 (Baldari et al. (1987) *Embo J.* 6: 229–234); pMFa (Kurjan and Herskowitz (1982) *Cell* 30: 933–943); JRY88 (Schultz et al. (1987) *Gene* 54: 113–123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in *E. coli*, suitable expression vectors include, among others, pTRC (Amann et al. (1988) *Gene* 69: 301–315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.* 64:3963–3966; and pSEM (Knapp et al. (1990) *BioTechniques* 8: 280–281). The use of pTRC, and pET-11d, for example, will lead to the expression of unfused protein. The use of pMAL, pRIT5 pSEM and pGEX will lead to the expression of peptide fused to maltose E binding protein (pMAL), protein A (pRIT5), truncated β-galactosidase (PSEM), or glutathione S-transferase (pGEX). When an osteopontin derived chemotactic peptide of the invention is expressed as a fusion protein, it is particularly advantageous to introduce an enzymatic cleavage site at the fusion junction between the carrier protein and osteopontin derived chemotactic peptide. The osteopontin derived chemotactic peptide may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant osteopontin derived chemotactic peptides in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli*, where such nucleic acid alteration would not affect the amino acid sequence of the expressed peptide.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be chemically synthesized using standard techniques (i.e. solid phase synthesis).

The present invention also provides nucleic acid sequences encoding peptides of the invention. Nucleic acid sequences used in any embodiment of this invention can be cDNA obtained from cDNAs encoding the corresponding peptide sequences, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of osteopontin derived chemotactic peptide, or fragments thereof, hybridizes, or 2) the sequence (or corresponding sequence portion) complementary to the nucleic acid sequences encoding the peptide sequence of osteopontin derived chemotactic peptide, a sequence which encodes a product (e.g., a peptide) having the same functional characteristics of the product encoded by the sequence (or corresponding sequence portion) of osteopontin derived chemotactic peptide. Whether a functional equivalent must meet one or both criteria will depend on its use (e.g., if it is to be used only as an oligoprobe, it need meet only the first or second criteria and if it is to be used to produce an osteopontin derived chemotactic peptide of the invention, it need only meet the third criterion).

The present invention also provides a method of producing isolated osteopontin derived chemotactic peptides of the invention or portions thereof comprising the steps of culturing a host cell transformed with a nucleic acid sequence encoding an osteopontin derived chemotactic peptide of the invention in an appropriate medium to produce a mixture of cells and medium containing said osteopontin derived chemotactic peptide; and purifying the mixture to produce substantially pure osteopontin derived chemotactic peptide. Host cells transformed with an expression vector containing DNA coding for an osteopontin derived chemotactic peptide of the invention or a portion thereof are cultured in a suitable medium for the host cell. Osteopontin derived chemotactic peptides of the invention can be purified from cell culture medium, host cells, or both using techniques known in the art for purifying peptides and proteins including ion-exchange chromatography, gel filtration chromatography, ultrafiltration, electrophoresis and immunopurification with antibodies specific for the osteopontin derived chemotactic peptides or portions thereof of the invention.

The invention also includes antibodies specifically reactive with osteopontin derived chemotactic peptides of the invention. Anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal such as a mouse, a hamster or rabbit can be immunized with an immunogenic form of the peptide. Techniques for conferring immunogenicity on a protein or peptide include conjugation to carriers or other techniques well known in the art. An immunogenic portion of the subject osteopontin derived chemotactic peptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of the osteopontin derived chemotactic peptide of the invention, e.g. antigenic determinants of peptide 51, peptide SP64 or the peptide of SEQ ID NO:1.

The term "antibody", includes fragments thereof which are also specifically reactive with an osteopontin derived chemotactic peptide. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments.

Both monoclonal and polyclonal antibodies (Ab) directed against the osteopontin derived chemotactic peptides, or fragments or analogs thereof, and antibody fragments such as Fab and $F(ab')_2$, can be used to block the action of osteopontin and allow the study of the role of the osptepontin derived chemotactic peptides of the present invention.

Antibodies which specifically bind osteopontin epitopes can also be used in immunohistochemical staining of tissue samples in order to evaluate the abundance and pattern of expression of osteopontin. Anti-osteopontin derived chemotactic peptide antibodies can be used diagnostically in immuno-precipitation and immuno-blotting to detect and evaluate wild type or mutant osteopontin polypeptide levels in tissue or bodily fluid as part of a clinical testing procedure. Likewise, the ability to monitor osteopontin levels in an individual can allow determination of the efficacy of a given treatment regimen for an individual afflicted with disorders associated with tumor metastases. The level of osteopontin can be measured in tissue, such as produced by biopsy.

Another application of anti-osteopontin derived chemotactic peptide antibodies of the present invention is in the immunological screening of cDNA libraries constructed in expression vectors such as 1gt11, 1gt18–23, 1ZAP, and 1ORF8. Messenger libraries of this type, having coding sequences inserted in the correct reading frame and orientation, can produce fusion proteins. For instance, 1gt11 will produce fusion proteins whose amino termini consist of β-galactosidase amino acid sequences and whose carboxy termini consist of a foreign polypeptide. Antigenic epitopes of a subject osteopontin derived chemotactic peptide can then be detected with antibodies, as, for example, reacting nitrocellulose filters lifted from infected plates with anti-osteopontin derived chemotactic peptide antibodies. Phage, scored by this assay, can then be isolated from the infected plate. Thus, the presence of osteopontin homologs can be detected and cloned from other animals, and alternate isoforms (including splicing variants) can be detected and cloned from human sources.

The invention also includes analogs, preferably biologically active analogs of the osteopontin derived chemotactic and inhibitory peptides of the invention. A biologically active analog is one having any in vivo or in vitro activity which is characteristic of the osteopontin derived chemotactic or inhibitory peptide of the invention, e.g., one or more of the biological activities described above. Most preferably the analog possesses about 40%, preferably about 70%, or at least about 90% of the activity of the osteopontin derived chemotactic or inhibitory peptide of the invention in any in vivo or in vitro chemotactic activity assay.

Analogs can differ from an osteopontin derived chemotactic peptide of the invention in amino acid sequence or in ways that do not involve sequence, or both. Non-sequence modifications include in vivo or in vitro chemical derivatization of an osteopontin derived chemotactic peptide of the invention. Non-sequence modifications include changes in acetylation, methylation, phosphorylation, carboxylation, or glycosylation.

It is also possible to modify the structure of a peptide of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity, or to which a component has been added for the same purpose.

For instance, non-hydrolyzable peptide analogs of such residues can be generated using benzodiazepine (see e.g., Freidinger et al. in Peptides: Chemistry and Biology, G. R. Marshall ed., ESCOM Publisher: Leiden, Netherlands, 1988), azepine (see e.g., Huffinan et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) *J. Med. Chem.* 29:295), -turn dipeptide cores (Nagai et al. (1985) *Tetrahedron Lett.* 26:647; and Sato et al. (1986) *J. Chem. Soc. Perkin. Trans.* 1:1231), and -aminoalcohols (Gordon et al. (1985) *Biochem. Biophys. Res. Commun.* 126:419; and Dann et al. (1986) *Biochem. Biophys. Res. Commun.* 134:71).

Natural peptide linkages can be replaced by a linkage selected from the group consisting of: —$CH_2NH$—, —$CH_2S$—, —$CH_2$—$CH_2$—, —$CH=CH$—(cis and trans), —$COCH_2$—, —$CH(OH)CH_2$—, and —$CH_2SO$—, by methods known in the art. A particularly preferred non-peptide linkage is —$CH_2NH$—.

Additionally, peptides of the invention can be modified by replacing an amino acid shown to be essential for chemotactic activity with another, preferably similar amino acid residue (conservative substitution) whose presence is shown to enhance, diminish but not eliminate or not affect chemotactic activity.

In order to enhance stability and/or reactivity, peptides of the invention can also be modified to incorporate one or more polymorphisms in the amino acid sequence of the peptide resulting from natural allelic variation. Additionally, D-amino acids, non-natural amino acids or non-amino acid analogues can be substituted or added to produce a modified peptide within the scope of this invention. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide. Furthermore, peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of peptides or portions thereof can also include reduction/alyklation (Tarr in: *Methods of Protein Microcharacterization*, J. E. Silver ed. Humana Press, Clifton, N.J., pp 155–194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939,239; or mild formalin treatment (Marsh *International Archives of Allergy and Applied Immunology*, 41:199–215 (1971)).

To facilitate purification and potentially increase solubility of peptides of the invention, it is possible to add reporter group(s) to the peptide backbone. For example, polyhistidine can be added to a peptide to purify the peptide on immobilized metal ion affinity chromatography (Hochuli, E. et al., *Bio/Technology*, 6:1321–1325 (1988)). In addition, specific endoprotease cleavage sites can be introduced, if desired, between a reporter group and amino acid sequences of a peptide to facilitate isolation of peptides free of irrelevant sequences.

Site-directed mutagenesis of DNA encoding a peptide of the invention can be used to modify the structure of the peptide by methods known in the art. Such methods may, among others, include PCR with degenerate oligonucleotides (Ho et al., *Gene*, 77:51–59 (1989)) or total synthesis of mutated genes (Hostomsky, Z. et al., *Biochem. Biophys, Res. Comm.*, 161:1056–1063 (1989)). To enhance bacterial expression, the aforementioned methods can be used in conjunction with other procedures to change the eucaryotic codons in DNA constructs encoding protein or peptides of the invention to ones preferentially used in *E. coli*, yeast, mammalian cells, or other eukaryotic cells.

Peptides or antibodies of the present invention can also be used for detecting inflammation. For example, this could be done by combining blood or blood products obtained from an individual with an isolated osteopontin derived chemotactic peptide, under conditions appropriate for binding of components in the blood (e.g., antibodies, T-cells, B-cells) with the peptide(s) and determining the extent to which such binding occurs.

The osteopontin derived chemotactic and inhibitory peptides of the invention can be used in methods of diagnosing, treating and preventing tumor metastasis, inflammation, osteoporosis and immune diseases. Thus the present invention provides therapeutic compositions comprising isolated peptides or analogs thereof produced in a host cell transformed to express such osteopontin derived chemotactic peptide or analogs thereof and a pharmaceutically acceptable carrier, or diluent. The therapeutic compositions of the invention may also comprise synthetically prepared osteopontin derived chemotactic peptides or analogs thereof and a pharmaceutically acceptable carrier or diluent. Administration of the therapeutic compositions of the present invention to an individual can be carried out using known techniques. Osteopontin derived chemotactic peptides or analogs thereof may be administered to an individual in combination with, for example, an appropriate diluent, adjuvant and/or a carrier. Pharmaceutically acceptable diluents include saline and aqueous buffer solutions. Pharmaceutically acceptable carriers include polyethylene glycol (Wie et al. (1981) *Int. Arch. Allergy Appl. Immunol.* 64:84–99) and liposomes (Strejan et al. (1984) *J. Neuroimmunol.* 7: 27). The carrier can also include a matrix, e.g., fibrin, collagen, gelatin, agarose, calcium phosphate containing compounds and combinations thereof. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether.

Administration of the therapeutic compositions of the present invention to an individual can be carried out using known procedures at dosages and for periods of time effective to significantly reduce or eliminate symptoms associated with the condition or disease being treated. Effective amounts of the therapeutic compositions will vary according to the age, sex, and weight of the "subject", and the ability of the osteopontin derived chemotactic peptide to perform its intended function.

The term "subject" is intended to include subjects susceptible to the particular condition or disease being treated. The term "subject" is intended to include mammals, particularly humans. An examples of a subject includes a mammal susceptible to metastatic disease, e.g., cancer. Another example of a subject includes a mammal capable of being wounded or a mammal with persistent, slow-healing wounds. For example, the therapeutic compositions can be administered to promote wound healing or prevent or inhibit metastasis of neoplastic cells.

In addition to compositions containing a single peptide, mixtures of at least two peptides (i.e., a physical mixture of at least two peptides) can also be provided. Such compositions can be administered in the form of a therapeutic composition with a pharmaceutically acceptable carrier or diluent. A therapeutically effective amount of one or more of such compositions can be administered simultaneously or sequentially. Preferred therapeutic compositions comprise peptides which include the peptides having the amino acid sequences shown in SEQ ID NOs:1–7. Dosage regima may be adjusted to provide the optimum therapeutic response. For example, several divided doses may be administered daily or the dose may be proportionally reduced as indicated by the exigencies of the therapeutic situation. A therapeutically effective amount is that amount sufficient to significantly reduce or alleviate symptoms associated with the particular condition or disease being treated. A preferred composition of the present invention is a wound healing composition. The wound healing composition contains a wound healing effective amount of osteopontin derived chemotactic peptide of the invention.

The active compound (i.e., peptide or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound.

To administer a peptide by other than parenteral administration, it may be necessary to coat the protein with, or co-administer the protein with, a material to prevent its inactivation. For example, peptide or portion thereof may be co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.* 7:27).

The active compound may also be administered parenterally or intraperitoneally. Dispersions can also be prepared in glycerol, liquid polyethyline glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions of dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glyceral, propylene glycol, and liquid polyetheylene glycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thirmerosal, and the like. In many cases, it will be preferable to include isotonic agents, for example, sugars, polyalcohols such as manitol and sorbitol or sodium chloride in the composition. Prolonged absorption of the injectable compositions can be brought about, including in the composition, an agent which delays absorption, for example, aluminum monostearate and gelatin.

Sterile injectable solutions can be prepared by incorporating active compound (i.e., peptide or fragment thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., peptide or fragment thereof) plus any additional desired ingredient from a previously sterile-filtered solution thereof.

When a peptide of the invention is suitably protected, as described above, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained.

The tablets, troches, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered topically. The use of a non-ageous lipid miscible carrier, for example, such as prepared with liposomes are particularly advantageous since they provide improved activity at the treatment site (e.g., the wound site).

The language "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. The language "dosage unit form" includes physically discrete units suited as unitary dosages for the mammalian subjects to be treated; each unit containing a predetermined quantity of active compound calculated to produce the desired therapeutic effect in association with the required pharmaceutical carrier. The specification for the novel dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The osteopontin derived chemotactic peptides of the invention or analogs thereof can be used to coat a prosthetic device. It is not necessary for the osteopontin derived chemotactic peptide of the invention to be covalently attached to the surface toward which chemotaxis is being stimulated. It is sufficient that the peptide be present at the surface. Therefore, the language "the incorporation of an osteopontin derived chemotactic peptide in the prosthetic device" includes all methods of applying an osteopontin derived chemotactic peptide of this invention to a surface, whether that application results in chemical bonding or not. For example, solutions or suspensions containing the peptide can be painted on the surface of a prosthetic device or a device can be submerged in a solution of the chemotactic peptide.

It is also possible to form covalent bonds between the osteopontin derived chemotactic peptide and the prosthetic device. For example, during the synthesis of an osteopontin derived chemotactic peptide as described above, various intermediates are produced which have reactive carboxy or amino terminals. Many of the prosthetic devices which are intended for incorporation into regenerating tissue are prepared from collagen or related materials and therefore contain free amino acid functional groups, such as amino or carboxylic acid groups. Peptide bonds can easily be formed between such functional groups in the prosthetic device and reactive intermediates such as those described above.

The type of prosthetic device which can be used in conjunction with the present invention is not limited, since the chemotactic property is related to the peptide and not to the prosthetic device itself. It is preferred however, that the prosthetic device be one which is intended for incorporation into regenerating tissue, such as an artificial vein or artery or artificial skin. Other useful prosthetic devices include artificial hips and artificial knees. The most commonly used fabric for blood vessel prosthesis is made from DACRON (Trademark, DuPont), a synthetic polyester fiber made from polyethylene terephthalate. DACRON has been used in several weaves and in combination with other materials. An example of a frequently used material is the DeBakey Elastic DACRON fabric manufactured by USCI, a division of C.R. Bard, Inc. (Cat. No. 007830). Other commonly used materials are felted polyurethane and polytetrafluorethylene (Berkowitz et al., *Surgery*, 72, 221 (1972); Wagner et al, *J. Surg. Ret.*, 1, 52 (1956); Goldfarb et al., *Trans Am. Soc. Art. Int. Org.*, XXIII, 268 (1977)). No chemotactic substance is normally used with these materials.

Another recent development in prosthetic devices is artificial skin of the type disclosed in Yannas and Burke, *J. Biomed. Mat. Res.*, 14.65–81 (1980). The artificial skin is a collagen/glycosaminoglycan (GAG) composite and had been successfully tested as full-thickness skin wound replacements. Such membranes have effectively protected wounds from infection and fluid loss for long periods of time without rejection and without requiring change or other invasive manipulation. Appropriately designed artificial skin of this type has retarded the wound contraction, and the artificial skin has been replaced, at least in part, by newly synthesized connective tissue. Additional disclosure of this artificial skin is found in Yannas et al., ibid, 107–131 (1980), and Dagalakis et al, ibid, 511–528 (1980). Two particularly preferred embodiments of the present invention involve using the chemotactic polypeptide with a collagen/glycosaminoglycan composite material as an artificial skin, as described in U.S. Pat. No. 4,280,954, and with biocompatible artificial materials based on polypeptides as described in U.S. Pat No. 4,187,852, all of which are herein incorporated by reference. These are peptide-containing materials, and the chemotactic polypeptide may readily be attached by covalent bonding into such materials by the methods described above. However, as also previously indicated, covalent bonding is not necessary and indeed is not preferred since the chemotactic property is also exhibited when the chemotactic peptide Is merely present on the surface or in the presence of a prosthetic material. Prosthetic devices having surfaces comprising other structural peptides are also preferred over prosthetic devices having other types of surfaces, although other types of surfaces, such as DACRON, and other synthetic fibers, are specifically included. Examples include natural materials such tendons or ligaments (for example, those transferred from one location to another within the same body) and synthetic or semi-synthetic materials. Semi-synthetic materials are those derived by manipulation of natural materials, such as collagen.

The amount of osteopontin derived chemotactic peptide which is required for a particular prosthetic device can be determined using art-recognized techniques. Generally, quite low concentrations of the chemotactic peptide are required. For example, doping of a non-chemotactic surface to produce low concentrations of 0.1 nM to 100 nM of an osteopontin derived chemotactic peptide of the invention at the surface will be sufficient.

Synthetically produced peptides of the invention comprising up to approximately forty-five amino acid residues in length, and most preferably up to approximately thirty amino acid residues in length are particularly desirable as increases in length may result in difficulty in peptide synthesis. Peptides of the invention may also be produced recombinantly as described above, and it is preferable that peptides of 45 amino acids or longer be produced recombinantly.

Therapeutic Uses

Antitumorigenic and Antimetastatic Uses

The compounds and/or peptides of the present invention are particularly useful for the prevention of metastasis of tumor cells. It is the ability to metastasize that makes cancers hard to eradicate surgically or by localized irradiation. To disseminate widely in the body, the cells of a typical solid tumor must be able to loosen their adhesion to their original neighbors, escape from the tissue of origin, burrow through other tissues until they reach a blood vessel or a lymphatic vessel, cross the basal lamina and endothelial lining of the vessel so as to enter the circulation, make an exit from the circulation elsewhere in the body, and survive and proliferate in the new environment in which they find themselves. Treatments which act at different stages of the metastasis process to prevent or inhibit spread of the tumor (neoplastic) cells are being developed. For example, it has been shown that for tumor cells to cross a basal lamina they must have laminin receptors, which enable the cells to adhere to the lamina, and they must secrete type IV collagenase, which helps them digest the lamina. Antibodies or other reagents that block either laminin attachment or the activity of type IV collagenase have been found to block metastasis in experimental animals.

Because tumor metastasis is dependent, at least in part, on an interaction between osteopontin and CD44 on tumor cells, blocking or inhibiting the CD44:osteopontin interaction is a valuable approach to inhibition of metastasis. In one embodiment, a compound for use in inhibition of metastasis includes an inhibitory compound or peptide. In another embodiment, a compound for use in inhibition of metastasis is a chemotactic compound or peptide. In such an embodiment, a chemotactic compound or peptide (e.g., an osteopontin-derived compound or peptide) can be used to competitively inhibit the interaction between osteopontin and CD44.

Immunogenic Uses

The compounds and/or peptides of the present invention can also be used to enhance an immune response. For example, a key component of an immune response (e.g., a Type 1 or cellular immune response) is the recruitment of macrophages to, for example, a site of infection. Accordingly, the chemotactic compounds and/or peptides (e.g., osteopontin-derived peptides) can be used to attract macrophages to promote the progression of an immune response. In particular, the chemotactic compounds and/or peptides are useful when one wishes to more rapidly promote macrophage recruitment. For example, during would healing, it may be desirable to more rapidly recruit macrophages to more rapidly close a wound. In this aspect, the chemotactic compounds and/or peptides of the present invention are particularly useful because they recruit macrophages to the size of administration more rapidly but, do not increase the total number of macrophages recruited. This feature prevents the harmful or unwanted side effects attributable to over-recruitment of macrophages, e.g., damage to the surrounding tissue.

A preferred application of this method is promotion of wound healing in a subject capable of being wounded or a subject with persistent, slow-healing wounds. Subjects with persistent, slow healing wounds include mammals, e.g., humans in advanced stages of diabetes who have circulatory problems which prevent proper wound healing of persistent wounds on the extremities, e.g., humans with severe wounds resulting from bums, e.g., humans with severely infected wounds.

Another example of a situation in which rapid recruitment of macrophages is desirable is in immunization. For example, rapid recruitment of macrophages at the site of immunization can enhances the immune response, in particular, aspects of the immune response dependent on macrophages (e.g., cytokine expression, production and secretion). Accordingly, the chemotactic compounds and/or peptides have a use as costimulatory molecules which are capable of contributing to amplification of the immune response.

Inhibition of Macrophage Recruitment

Yet another feature of the present invention, is the ability of the inhibitory compounds and/or peptides to block microphage recruitment. Instances in which the inhibitory compounds are particularly useful include the disruption of granulomas (a condition associated with many diseases resulting from the presence of too many macrophages which continuously secrete cytokines, resulting in disruption of the surrounding tissue. Yet another situation in which the inhibitory compounds and/or peptides are useful is in granulomatous inflammation. The inhibitory compounds and/or peptides can also be used to prevent connective tissue damage associated with the excess recruitment of macrophages. For example, in the instance of ruptured or leaking breast implants, the leakage of silicone is known to attracted phagocytes (to phagocytose the leaked silicone). The recruited phagocytes secrete proteases, $H_2O_2$, end superoxide, resulting in the recruiting of aditional macrophages which destroys the normal tissue. Yet another situation in which the inhibitory compounds and/or compounds have therapeutic utility is in Glomerulonephritis. The inhibitory compounds and/or peptides can suppress macrophage-mediated renal injury. Progressive renal injury (macrophage accumulation in the kidney) leads to histological damage including glomerular crescentic formation and tubulointerstitial fibrosis, each of which can be downregulated by inhibition of macrophage attraction and/or accumulation.

Angiogenesis and Angiogenic Disorders

The osteopontin derived chemotactic peptides of the invention can also be used for treating or preventing an angiogenic-associated disease. The process of angiogenesis, the growth of blood vessels, is fundamental to reproduction, development and repair. Under these conditions, angiogeneis is highly regulated and of short duration. In many pathologic states, the regulation is deranged so that the disease itself is driven by persistent, unabated neovascularization. Thus, tumor growth and metastasis are angiogenesis-dependent and a wide-variety of non-neoplastic diseases are dominated by uncontrolled angiogenesis. The language "angiogenic-associated disease" includes a disease or a condition resulting from unregulated, e.g., uncontrolled, growth of blood vessels. The term is intended to include both neoplastic and non-neoplastic diseases or conditions. For example, angiogenic-associated diseases include arthritis, psoriasis, hemangioma, cancer or tumor, e.g., solid tumor, metastasis, and ocular neovascularization.

The marked induction of osteopontin during arterial wound healing and tumor invasion and metastasis, suggests a role for this protein in these processes. Thus, the osteopontin derived chemotactic peptides of the invention can be used for stimulation or inhibition of angiogenesis. For example, antagonists of an osteopontin derived chemotactic peptide of the invention or antibodies raised against the osteopontin derived chemotactic peptides of the invention can be used as angiogenesis inhibitors in treatment of cancer, e.g., as: (1) adjuvant therapy; (2) prophylactic therapy to prevent tumor recurrence; or (3) anti-metastatic therapy.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following Examples which in no way should be construed as further limiting. The entire contents of all of the references (including literature references, issued patents, and published patent applications) cited throughout this application are hereby expressly incorporated by reference.

Exemplification

EXAMPLE 1

Peptide Mapping of Chemotactic Domain on Osteopontin by Tryptic Digest

Purified OPN (~0.5 mg) was digested with trypsin (2% w/w) in 0.2 ml of 50 mM $NH_4HCO_3$, pH 8.0, for 20 hours at 37° C. before treatment of the reaction products with 50 µl of 100% $H_2O$+0.1% trifluoroacidic acid (TFA) and resolution of the peptides by HPLC chromatography on C-18 column (25×0.46 cm). After injection the column was washed for 10 min, followed by linear gradient elution from 100% $H_2O$+0.1% TFA to 60% $CH_3CN$+0.55% TFA over 120 min, with a second gradient from 60% $CH_3CN$ to 80% $CN_3CN$ over 30 min at a flow rate of 0.5 ml/min. The absorbance at 219 nm was recorded continuously by an on-line chart recorder/integrator using Gilson HM Holochrome detector, and fractions of 0.5 ml were collected. This procedure results in the generation of partial tryptic peptides. This is essential to ensure that a chemotactic peptide containing an Arg or Lys residue will be detected by the assay and eliminates the necessity to do multiple digests with various proteases to ensure that all possible peptides were tested.

Each peak was then tested for mediation of chemotaxis or for its ability to inhibit OPN mediated chemotaxis using the chemotactic assay as follows (see e.g., Weber et al. (1996) *Science* 271:509–512). Briefly, uncoated polycarbonated filters (pore size 8 µM) were used to separate the upper and lower chambers of chemotactic wells. $1×10^3$ MDA-MB-231 cells ($CD44^+$human breast adenocarcinoma cells) were added to the upper chamber and incubated in the presence or absence of the indicated 50 pmols peptide. After 4 hours, the filters were removed, fixed in methanol arid stained with hematoxylin and eosin. Cells which have responded to the peptide, migrate to various areas of the lower surface and can be counted microscopically. Each data point is reported as the mean number of migrating cells per random high power field. The results are outlined in Table 1.

TABLE 1

Chemotactic Properties of Osteopontin Peptides

| | | Lower Chamber | | | | | |
|---|---|---|---|---|---|---|---|
| | | PBS | peptide 49 | peptide 50 | peptide 51 | peptide 52 | peptide 53 |
| Upper Chamber | PBS | 9 | 15 | 23 | 68* | 48 | 18 |
| | peptide 49 | 8 | 11 | 19 | 83* | 39 | 15 |
| | peptide 50 | 6 | 17 | 22 | 56* | 28 | 11 |
| | peptide 51 | 13 | 15 | 16 | 32 | 16 | 19 |
| | peptide 52 | 5 | 19 | 31 | 78* | 22 | 9 |
| | peptide 53 | 9 | 13 | 24 | 62* | 39 | 10 |

*= p, 0.05

Peptide 51 was identified as being chemotactic. The peptide was sequenced using a gas-phase sequenator and determined to have the sequence LVLDPK (SEQ ID NO:1). To confirm that chemotaxis was due to this peptide, a 16 amino acid peptide spanning the chemotactic sequence in OPN was synthesized and tested for its chemotactic properties. The resulting peptide, SP64 has the sequence KFHS-HKDKLVLDPKSK (SEQ ID NO:2) and containing the chemotactic sequence from residues 9–14. $2×10^4$ MDA-MB-231 cells were assayed for chemotactic response to the indicated peptides as described above. Table 2 sets forth the results. Each data point is reported as the mean number of migrating cells per six random high powered fields ± standard error of the mean. Each experiment was repeated four times.

TABLE 2

Chemotactic Properties of Synthetic Peptides

| | | Upper Chamber | | | | |
|---|---|---|---|---|---|---|
| | | PBS | pep 51 | SP64 | OPN | Ab64 |
| Lower Chamber | PBS | 9 | 6 | 243 | 23 | 5 |
| | Pep 51 | 248 | 65 | 109 | 48 | 21 |
| | SP64 | 217 | 97 | 66 | 66 | 25 |
| | OPN | 214 | 44 | 187 | 16 | 36 |

OPN = osteopontin 200 ng of bone OPN significantly (p<0.01) stimulated the chemotactic response of MDA-MB231, as did SP64 and pep 51. The migration of cells to the lower side of the filter in response to chemotactic agent and the inhibition of chemotaxis by addition of chemotactic agent to the upper chamber supports the conclusion that the observed phenomena is chemotaxis and not random migration. Several additional cell types, e.g., smooth muscle cells, endothelial cells, macrophages, breast carcinoma cells, colon carcinoma cells, adenocarcinoma cells and osteoprogenitor cells, were also tested for their ability to chemotax to peptide 51.

SP64 was conjugated to BSA and polyclonal antibodies were raised in rabbits. The resulting plasma containing antibodies against the synthetic peptide was purified by affinity chromatography on a sepharose 4B column conjugated with the relevant peptide. The resulting affinity purified antibody was then tested for its ability to inhibit the chemotaxis of to OPN. As demonstrated by the data in the last column of Table 2, anti-SP64 antibody (Ab64) inhibited the chemotactic response of MDA-MB-231. In a similar fashion, 1 μg of affinity purified rabbit anti-mouse osteopontin antibody and 1 μg of monoclonal antibody against human CD44 inhibited the chemotactic response of MDA-MB-231. It is assumed that the antibody complexes with the chemotactic domain and prevents its recognition by the chemotactic receptor.

EXAMPLE 2

Mutational Analysis

To test the amino acid specificity for chemotactic response several substitutions were created in the chemotactic sequence and the new peptides tested for their ability to induce chemotaxis. The results are summarized in Table 3. Data are expressed as migratory index (cells migrating in response to peptide/cells migration in response to LVLDPK, SEQ ID NO:1).

TABLE 3

Sequence Specificity of OPN-derived Chemotactic Peptides

| | Chemotactic Peptides | Migratory Index | SEQ ID NO: |
|---|---|---|---|
| peptide 51 | LVLDPK | 1 | 1 |
| SP64 | KFHSHKDKLVLDPKSK | 1 | 2 |
| pepA | LVLVPK | 0.2 | 8 |
| pepB | LVPDPK | 1 | 9 |
| pepC | LVPDSK | 1 | 5 |
| pepD | LVIDPK | 1 | 6 |
| pepE | LVLDEK | 0.2 | 10 |
| pepF | VLDPK | 0.7 | 7 |
| pepG | LVLDP | 0.1 | 11 |
| pepH | LELDPK | 0.3 | 12 |
| pepI | LVLAPK | 0.1 | 13 |
| pepJ | LVLEPK | 0.6 | 14 |
| pepK | LVLDPA | 0.1 | 15 |
| pepJ' | VLEP | 0.1 | 16 |
| pepK' | ILVVDPK | 1.0 | 17 |

Additional peptides which have been tested and shown to have chemotactic activity include VVLDPK (SEQ ID NO:18), ILVDPK (SEQ ID NO:19), and LLVDPK (SEQ ID NO:20). Likewise, a Shortened peptide including VDPK (SEQ ID NO:21) and VLDSK (SEQ ID NO:22) have also been demonstrated to retain chemotactic activity. These results clearly indicate that changing the aspartate (D) to an amino acid other than an acidic amino acid results in total loss of biological activity. Replacing D with glutamate results in 50% loss of activity. Similarly replacing the terminal Lysine with alanine also results in total loss of activity.

To evaluate the potential of peptide analogues to inhibit OPN induced chemotaxis, 100 nmoles of peptide was added to the lower compartment and the response of these cells to OPN was determined as described. MI(buffer) was calculated by dividing the number of cells migrating in response to peptide by the number of cells migrating in response to buffer. MI(inhibitory) equals the number of cells migrating towards OPN in the presence of buffer divided by the number migrating towards OPN in the presence of peptide.

TABLE 4

Inhibitory Activity of OPN-derived Peptides

| Chemotactic Peptides | | MI | MI buffer | MI inhibitory | SEQ ID NO: |
|---|---|---|---|---|---|
| Pep51 | LVLDPK | 1 | 10 | 10 | 1 |
| SP64 | KFHSHKDKLVLDPKSK | 1 | 12 | 9 | 2 |
| pepA' | LVVDPK | 1 | 9 | 8 | 8 |
| pepB' | LVPDPK | 1 | 10 | 8 | 9 |
| pepC | LVPDSK | 1 | 7 | 10 | 5 |
| pepD | LVIDPK | 1 | 11 | 9 | 6 |
| pepE | LVLDEK | 0.2 | 2 | 10 | 10 |
| pepF | VLDPK | 0.7 | 6 | 7 | 7 |
| pepG | LVLDP | 0.1 | 0 | 4 | 11 |
| pepH | LELDPK | 0.3 | 2 | 10 | 12 |
| pepI | LVLAPK | 0.1 | 1 | 9 | 13 |
| pepJ | LVLEPK | 0.6 | 6 | 9 | 14 |
| pepK" | Acetyl-LVLDP | — | 1 | 4 | 23 |
| pepL | Acetyl-MLDP | — | 1 | 2 | 24 |
| pepM | Acetyl-HKDKMLDP | — | 0.8 | 2 | 25 |

These data support the characterization of essential residues described above. Changing the aspartate (D) to an amino acid other than an acidic amino acid results in loss of biological activity. A hydrophobic tail is necessary for the biological activity of the peptide. The C-terminal K is essential, however, arginine can partially substitute for it. The proline can be replaced by any other amino acid that can adopt a turn conformation. Acetylation of the N-terminal has little effect on the biological activity of the peptide.

Moreover, by determining the migratory index against peptide 51, it was discovered that the peptide LVLDP (SEQ ID NO:11), having the basic residue (e.g., lysine) truncated rather than substituted inhibits chemotaxis as compared to being merely inactive. Subsequently it has been determined that the peptide VLEP (SEQ ID NO:16) is also inhibitory for chemotaxis. In particular, it has been determined that the peptide VLEP (SEQ ID NO:16) inhibits macrophage recruitment by osteopontin, C5a and by fibrorectin.

EXAMPLE 3

In Vivo Cellular Migration

Boyden chamber experiments have indicated that osteopontin elicits a migration of a cellular population predominantly comprised of Mac-1$^+$CD44$^+$ cells. Thus, it was investigated whether a similar population of cells was attracted in vivo following intraperitoneal injection with osteopontin.

Mice were injected intraperitoneally with varying dosages of K7 osteosarcoma-derived osteopontin. All injection volumes were 200 μl. Injections of vehicle alone (PBS) served as negative controls and vehicle plus 20 μg lipopolysaccharide (LPS) injections served as positive controls for elicitation of peritoneal exudates.

Mice were sacrificed by $CO_2$-asphyxiation at varying times following injection. Immediately after sacrifice, peritoneal exudate was recovered by intraperitoneal injection and recovery of 10 mL PBS. The lavage procedure was performed twice on each mouse. Following this, red blood cells were lysed by hypotonic lysis with ACK lysis buffer (0.15 M $NH_4Cl$, 1.0 mM $KHCO_3$, 0.1 mM $Na_2EDTA$, pH 7.4) for 5 minutes at room temperature, and the preparation was washed in DMEM, 5% FBS. Cells were resuspended in DMEM, 5% FBS for fluorescent antibody staining.

Each sample of cells to be analyzed for specific surface markers was suspended in DMEM, 5% FBS at a concentration of 0.2 to 1 million cells in 50 μl. Fluorescence-labeled antibodies were added at 1 μg/1×10⁶ cells, and incubated with the cells for 30 minutes at 4° C. Samples were washed twice with 200 μl of PBS following antibody staining and fixed with 500 μl of 2% paraformaldehyde in PBS. Peritoneal exudate cells were analyzed by dual-color flow cytometry for expression of CD44 (PE), CD 11 b (Mac-1, FITC, macrophage marker), B220 (FITC, B-cell marker), and CD3 (FITC, T-cell marker). All antibodies were purchased from PharMingen and flow cytometric analysis was done using a Coulter EPICS flow cytometer. Controls for non-specific binding and single color controls were included.

Titration of soluble osteopontin into the peritoneum resulted in a dose dependent increase in the cellular infiltrate 6 hours after injection, with a peak response occurring at a dose around 13 μg. The number of Mac-1+ cells in the infiltrate increased fivefold over basal levels during this time while the number of CD3+ and B220+ cells was only marginally elevated. A nearly sixfold reduction in number of CD44+ Mac1+ cells also occurred at a dose around 7 μg, forming a relatively sharp peak response that decreased at higher doses. Preferential attraction of Mac1+ and CD44+ cells at a relatively low dosage indicates that i.p. inoculation of osteopontin at this level is likely to elicit a lineage-specific chemotactic response as opposed to a generalized inflammatory response. These data support the observations made in the in vitro splenocyte chemotaxis assays that the predominant cell population to migrate in response to phosphorylated osteopontin is comprised of Mac-1+ CD44+ cells.

To further characterize the effects of osteopontin on in vivo cellular migration, a time course experiment was performed using an osteopontin dosage that elicited peak levels of infiltration. The total cellular response to osteopontin administration peaked sharply at 4 to 6 hours. This is likely to be due to a high rate of clearance from the peritoneal cavity. Co-injection of osteopontin with anti-osteopontin antibody described herein in Example 3 prevented the influx of cells whereas rabbit immunoglobulin had no effect (PBS 178 250 cells, OPN 1.16 million cells, OPN+anti-OPN 534 750 cells, OPN +Ig 922 250 cells, PBS+Ig 496 000 cells). The ability of the anti-osteopontin antibody to diminish the observed chemotactic response in vivo demonstrates the in vivo specificity of osteopontin.

EXAMPLE 4

Since the peptide LVLDPK (SEQ ID NO:1) was chemotactic to tumor cells and macrophages in vitro, we tested whether the peptide was chemotactic in vivo. 25 nmols of the peptide were injected into the peritoneal cavity of C57 black mice. After six hours the cells recruited into the peritoneum were recovered by lavage and identified by flow cytometry. Titration of soluble peptides into the peritoneum induces a cellular infiltrate in a dose dependent manner. The induction ratio is the number of cells of a particular lineage recovered from the peritoneum of a peptide-injected mouse (e.g., 6 hours after injection) normalized for each experiment to the number of cells of the same lineage recovered from the peritoneum of a PBS-injected mouse. Cell numbers for PBS-injected mice ranged from 443,00 to 646,000 cells total; 182,300 to 325,000 CD44⁺ cells; 224,000 to 496,000 Mac-1⁻ cells; 31,300 to 76,000 B220⁺ cells; 18,100 to 21,100 CD3⁺ cells), representing the induction of macrophages (Mac-1⁺), B cells (B220⁺), and T cells (CD3⁺). Values represent an average of 6 mice.

TABLE 5

Chemotactic Activity of LVLDPK (SEQ ID NO: 1) in vivo

| | SEQ ID NO: | Total | Total CD44 | Mono-cytes | B-lymphocytes | T-lymphocytes |
|---|---|---|---|---|---|---|
| PBS | | 1 | 1 | 1 | 1 | 1 |
| OPN | | 11.3 | 9.6* | 10.4* | 1.2 | 1 |
| LVLVPK | 8 | 1.3 | 1.8 | 1.2 | 1 | 1.1 |
| LVLDPK | 1 | 8.6* | 7.9* | 7.1* | 1.3 | 1.3 |
| VLDPK | 7 | 4 | 3.1 | 2.8 | 1.1 | 0.8 |

*$p < 0.05$

The results presented in Table 5 demonstrate that LVLDPK (SEQ ID NO:1) was chemotactic to macrophages in vivo and that replacing the aspartate with alanine in the sequence completely eliminated this activity. A truncated version of LVLDPK (SEQ ID NO:1), namely VLDPK (SEQ ID NO:17), was also chemotactic but exhibited less activity perhaps due to the faster clearing rate of the peptide. When the peptide Ac-MLDP (SEQ ID NO:24) was tested in similar assays in vivo, it totally abolished the chemotactic response to OPN of LVLDPK (SEQ ID NO:1) when coinjected with the chemotactic agent.

EXAMPLE 5

Treatment of breast cancer cells with pepL or pepM resulted in activation of apoptosis. One million MDA-MB-231 cells were incubated with 100 nM of the OPN, LVVDPK (SEQ ID NO:8), Ac-MLDP (SEQ ID NO:23) or Ac-HKDKMLDP (SEQ ID NO:24) in DME containing 10% FBS in a humidified atmosphere of 5% CO2 at 370° C. After 12 hours, Caspase 8 and the % of apoptotic cells were determined. Caspase was determined by a fluorescent assay using Chemicon's FLICE/Caspase-8 Fluorometric Protease Assay Kit as described by the manufacturers. Apoptosis was determined using TUNEL using the "In situ Cell Death Detection Kit" (Boehringer-Mannheim, Germany). Ac-MLDP (SEQ ID NO:24) resulted in an 80% increase in apoptosis as compared to OPN. Ac-HKDKMLDP (SEQ ID NO:25) resulted in an ~120% increase. Ac-MLDP (SEQ ID NO:24) and Ac-HKDKMLDP (SEQ ID NO:25) likewise resulted in an ~65% and an ~80% increase In Caspase 8 activity, respectively. The control peptide LVVDPK (SEQ ID NO:8) resulted in virtually undetectable apoptosis or Caspase 8 activity.

Moreover, treatment of breast cancer cells with pepL resulted in increased NO production. The production of nitric oxide (NO) by the breast tumor cells was assessed 12 hours after incubation in the presence of pepL by measuring the accumulation of nitrate in culture supernatants. Griess reagents were used as described by Hwang et al. (1993).

These results implicate chemotactic inhibitory agents in activation cell death cancer cells and supports use of such agents to therapeutically treat susceptible tumors. Peritoneal macrophages, fibroblasts or osteoblasts treated with PepM did not undergo apoptosis, indicating that the this activation of cell death is specific and possibly receptor mediated.

Moreover, several reports have correlated NO production (by a variety of mechanisms) with tumor death (Boggio et al., 1998; Janssen and Van den Berge., 1998). The data presented here further implicate this pathway in the inhibition of tumor growth and metastasis.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A purified osteopontin-derived peptide, wherein the peptide inhibits chemotaxis, is at least 4 amino acids long and is identical to at least a 4 amino acid sequence found in osteopontin.

2. A purified osteopontin-derived peptide having chemotaxis-inhibitory activity, wherein the peptide is at least 4 amino acids long and is identical to at least a 4 amino acid sequence found in osteopontin.

3. A purified peptide having chemotaxis-inhibitory activity and having a hydrophobic core constituent consisting of an amino acid sequence selected from the group consisting of LVLDP (SEQ ID NO:11), VLEP (SEQ ID NO:16), Acetyl-LVLDP (SEQ ID NO:23), Acetyl-MLDP (SEQ ID NO:24), and Acetyl-HKDKMLDP (SEQ ID NO:25).

4. A therapeutic composition comprising the peptide of claim 3 and a pharmaceutically-acceptable carrier or diluent.

5. The composition claim 4, wherein said carrier is a matrix.

6. The composition of claim 5, wherein said matrix is selected from the group consisting of fibrin, collagen, gelatin and agarose.

* * * * *